US 6,730,387 B2
(12) United States Patent
Rezai et al.

(10) Patent No.: US 6,730,387 B2
(45) Date of Patent: *May 4, 2004

(54) ABSORBENT MATERIALS HAVING IMPROVED STRUCTURAL STABILITY IN DRY AND WET STATES AND MAKING METHODS THEREFOR

(75) Inventors: Ebrahim Rezai, Kobe (JP); Kesyin Hsueh, Kobe (JP)

(73) Assignee: The Procter & Gamble Company, Cincinnati, OH (US)

(*) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 09/171,049
(22) PCT Filed: Apr. 24, 1997
(86) PCT No.: PCT/US97/06603
  § 371 (c)(1),
  (2), (4) Date: Oct. 12, 1998
(87) PCT Pub. No.: WO97/39780
  PCT Pub. Date: Oct. 30, 1997
(65) Prior Publication Data
  US 2003/0060112 A1 Mar. 27, 2003

(30) Foreign Application Priority Data
Apr. 24, 1996 (JP) .......................................... H8-102736

(51) Int. Cl.$^7$ ........................... D06N 7/04; B32B 27/04; B32B 5/02; D04H 1/00
(52) U.S. Cl. ...................... 428/141; 428/143; 442/118; 442/340; 442/344; 442/409; 442/417
(58) Field of Search ........................ 604/368; 428/141, 428/304.4; 442/327, 340, 118

(56) References Cited

U.S. PATENT DOCUMENTS

| | | | |
|---|---|---|---|
| 3,669,103 A | 6/1972 | Harper et al. ................ 128/156 |
| 3,670,731 A | 6/1972 | Harmon ..................... 128/284 |
| 3,860,003 A | 1/1975 | Buell ........................ 128/287 |
| 4,062,817 A | 12/1977 | Westerman .......... 260/17.45 G |
| 4,076,663 A | 2/1978 | Masuda et al. ...... 260/17.4 GC |
| 4,093,776 A | 6/1978 | Aoki et al. .................... 428/402 |
| 4,285,343 A | 8/1981 | McNair ....................... 128/287 |
| 4,468,428 A | * 8/1984 | Early et al. ................. 428/221 |
| 4,608,047 A | 8/1986 | Mattingly .................... 604/387 |
| 4,666,983 A | 5/1987 | Tsubakimoto et al. ....... 525/119 |
| 4,687,478 A | 8/1987 | Van Tillburg ............... 604/387 |
| 4,695,278 A | 9/1987 | Lawson .................. 604/385 A |

(List continued on next page.)

FOREIGN PATENT DOCUMENTS

| | | | |
|---|---|---|---|
| EP | 156160 A2 * | 2/1985 | .......... A61L/15/00 |
| EP | 493011 * | 1/1992 | .......... A61L/15/60 |
| EP | 0 493 011 A2 | 7/1992 | |
| EP | 0 612 533 A1 | 8/1994 | |
| WO | WO 95/22356 | 8/1995 | |
| WO | WO 95/26209 | 10/1995 | |

*Primary Examiner*—Arti R. Singh
*Assistant Examiner*—Christopher Pratt
(74) *Attorney, Agent, or Firm*—Eileen L. Hughett; Edward J. Milbrada; Kirsten K. Stone

(57) ABSTRACT

An absorbent material having substantially improved structural stability in the dry and wet states. The absorbent materials are significantly less susceptible to handling losses of absorbent gelling particles during manufacturing operations. The absorbent material also is not subject to shifting of the absorbent gelling particles during or after swelling by fluids. The absorbent material comprises absorbent gelling particles comprising (a) a water-insoluble absorbent hydrogel-forming polymer; (b) a polycationic polymer bonded to the absorbent gelling particles at the surface thereof; (c) glue microfibers dispersed in the absorbent gelling particles; and (d) a carrier layer bonded to the absorbent gelling particles through the glue microfibers. The invention further relates to a method of making the absorbent materials, and the absorbent articles comprising the absorbent materials.

22 Claims, 1 Drawing Sheet

U.S. PATENT DOCUMENTS

| | | | |
|---|---|---|---|
| 4,734,478 A | 3/1988 | Tsubakimoto et al. | 527/300 |
| 4,808,178 A | 2/1989 | Aziz et al. | 604/385.2 |
| 4,816,025 A | 3/1989 | Foreman | 604/385.2 |
| 4,834,735 A | 5/1989 | Alemany et al. | 604/368 |
| 4,842,666 A | 6/1989 | Werenicz | 156/161 |
| 4,888,093 A | 12/1989 | Dean et al. | 162/157.6 |
| 4,889,596 A | 12/1989 | Schoggen et al. | 162/157.6 |
| 4,889,597 A | 12/1989 | Bourbon et al. | 162/157.6 |
| 4,898,642 A | 2/1990 | Moore et al. | 162/157.6 |
| 4,898,647 A | 2/1990 | Luce et al. | 204/13 |
| 5,151,092 A | 9/1992 | Buell et al. | 604/385.2 |
| 5,542,941 A | 8/1996 | Morita | 604/385.1 |
| 5,645,542 A * | 7/1997 | Anjur et al. | 604/368 |
| 5,669,894 A * | 9/1997 | Goldman et al. | 604/368 |
| 5,733,629 A * | 3/1998 | Insley | 428/141 |
| 5,849,405 A * | 12/1998 | Wang et al. | 428/304.4 |

* cited by examiner

ABSORBENT MATERIALS HAVING IMPROVED STRUCTURAL STABILITY IN DRY AND WET STATES AND MAKING METHODS THEREFOR

FIELD OF THE INVENTION

The present invention relates to absorbent materials that, upon contacting liquids such as water or body fluids, swell and imbibe such liquids. More specifically, the present invention relates to improved structural stability in the dry and wet states of absorbent materials. The absorbent material of the present invention has particular applicability to absorbent articles such as diapers, adult incontinence pads, sanitary napkins, and the like.

BACKGROUND

Water-insoluble, water-swellable, hydrogel-forming absorbent polymers are capable of absorbing large quantities of liquids such as water, body fluids (e.g., urine, blood, menstrual fluid), industrial fluids and household fluids and are further capable of retaining such absorbed liquids under moderate pressures. These absorption characteristics of such polymer materials make them especially useful for incorporation into absorbent articles such as disposable diapers, adult incontinence pads and briefs, and catamenial products such as sanitary napkins, and the like.

The development of highly absorbent members used in such absorbent articles are the subject of substantial commercial interest. A highly desired characteristic for such absorbent articles is thinness. For example, thinner diapers are less bulky to wear, fit better under clothing, and are less noticeable. They are also more compact in the package, making the diapers easier for the consumer to carry and store. Compactness in packaging also results in reduced distribution costs for the manufacturer and distributor, including less shelf space required in the store per diaper unit.

The ability to provide thinner absorbent articles such as a diaper has been contingent on the ability to develop relatively thin absorbent cores or structures that can acquire and store large quantities of discharged body fluids, particularly urine. In this regard, the use of certain absorbent polymers often referred to as "hydrogels" "superabsorbents" or "hydrocolloid" material, has been particularly important. See, for example, U.S. Pat. No. 3,699,103 (Harper et. al), issued Jun. 13, 1972, and U.S. Pat. No. 3,670,731 (Harmon), issued Jun. 20, 1972, that disclose the use of such absorbent polymers (hereafter "water-insoluble absorbent hydrogel-forming polymers") in absorbent articles.

Moreover, prior absorbent articles have generally comprised relatively low amounts (e.g., less than about 50% by weight) of absorbent gelling particles of the WAHPs. See, for example, U.S. Pat. No. 4,834,735 (Alemany et. al), issued May 30, 1989. It discloses that an absorbent structure or core contains preferably from about 9 to about 50% of WAHP in the fibrous matrix. Unfortunately several problems are encountered when one attempts to provide a thin absorbent core having more than 50% concentration of absorbent gelling particles by weight.

Conventional absorbent articles have the limitation that the absorbent gelling particles are not immobilized and are free to migrate(shift) during the manufacturing process and/or use(wearing). Migrations(shifting) of the absorbent gelling particles during manufacture can lead to absorbent material handling losses during manufacturing operations as well as nonhomogerous incorporation of the particles being used. A more significant problem, though, occurs when these absorbent gelling particles of WAHPs migrate during or after swelling. This inability to fix the particles at optimum locations leads to an insufficient urine storage capacity in one area and over-capacity in other areas due to the lack of stability.

One important factor is to minimize and/or eliminate the shifting of particles of WAHPs from the first applying location to another position and handling losses during manufacture.

One problem encountered is the shifting and/or leakage of swollen (e.g., with urine) particles of WAHP due to wear-related movement and pressure on the absorbent article. The inability to fix the particles at optimum location is another issue that results in insufficient urine storage capacity in one area and over-capacity in other areas. Subsequently the absorbent article will leak during use. The shifting of wet particles of WAHPs can cause core shifting and more incidence of gel leakage when in use, especially from an absorbent material containing high concentration of WAHPs.

Yet another important factor that has to be considered is the liquid permeability of WAHPs. It has been discovered that the permeability or flow conductivity of the gel layer formed by swelling in the presence of body fluids is extremely important when these absorbent polymers are used in absorbent cores or members at a high concentration in localized or throughout regions thereof. It should be noted that lack of liquid permeability or flow conductivity of absorbent polymers may directly impact on the ability of resultant gel layers to acquire and distribute body fluids.

Still another concern of WAHPs used in thinner absorbent article is the jelly and mushy feel when touching and handling the absorbent article after usage. When WAHP is dispersed in region or regions at a high concentration, the swollen gel formed by absorbing body fluids is a gel layer, in which the particulate is mobile and the gel layer collapses when subjected to forces such as pushing, squeezing, etc. when handling the absorbent article after usage. This is why absorbent articles having high concentration of WAHP give users or consumers "wet/mushy" feel when touching or handling them from outside.

Therefore, the present invention seeks to resolve the above problems by providing an absorbent material having improved structural stability in dry and wet status.

SUMMARY

Briefly stated, the present invention relates to absorbent materials having improved structural stability in dry and wet states. These absorbent materials comprise (a) absorbent gelling particles comprising a water-insoluble absorbent hydrogel-forming polymer; (b) a polycationic polymer; (c) glue microfibers; and (d) a carrier layer; wherein the polycationic polymer is bonded to the absorbent gelling particles; and the glue microfibers act as an adhesive between the absorbent gelling particles and the carrier layer. Because the glue microfibers are tacky, the absorbent gelling particles comprising a WAHP fix to the desired location on the carrier layer and do not shift to the another area in dry state. In wet state, when the absorbent material contacts liquids such as body fluids, the absorbent gelling particles contained in the absorbent material fix to the location first applied due to bonding of the polycationic polymer to the absorbent gelling particles comprising a WAHP, and the absorbent material does not shift.

The bonds between the absorbent gelling particles to the glue microfibers, which in turn, are bonded to the carrier layer, prevent the absorbent gelling particles from shifting during the manufacturing process. The polycationic polymer bonded to the absorbent gelling particles prevents the particles from shifting after they swell with liquid. Consequently, the absorbent material of the invention has improved liquid acquisition speed and low rewetness when in use. It has been found that when the absorbent material is contacted with liquids, the absorbent material swells, imbibes such liquids into the absorbent gelling particles, and absorbs even under moderate confining pressures.

In a preferred embodiment of the present invention, the carrier layer is selected from the group consisting of a woven material and a nonwoven material.

These absorbent materials may further comprise the cellulose fibers dispersed in the absorbent gelling particles, wherein the cellulose fibers are adhered to the absorbent gelling particles by the glue microfibers.

Preferably, the absorbent material of present invention comprises from about 50% to about 90% of the absorbent gelling particle, from about 0.1% to about 10% of the polycationic polymer, from about 1% to about 10% of the thermoplastic polymeric microfiber and from about 5% to about 50% of the carrier layer by weight.

The invention further relates to a method of make the absorbent materials, and the absorbent articles comprising the absorbent materials.

These and other features, aspects, and advantages of the present invention will become better understood with regard to the following description, attended claims and accompanying drawing.

DETAILED DESCRIPTION

Figure 1:
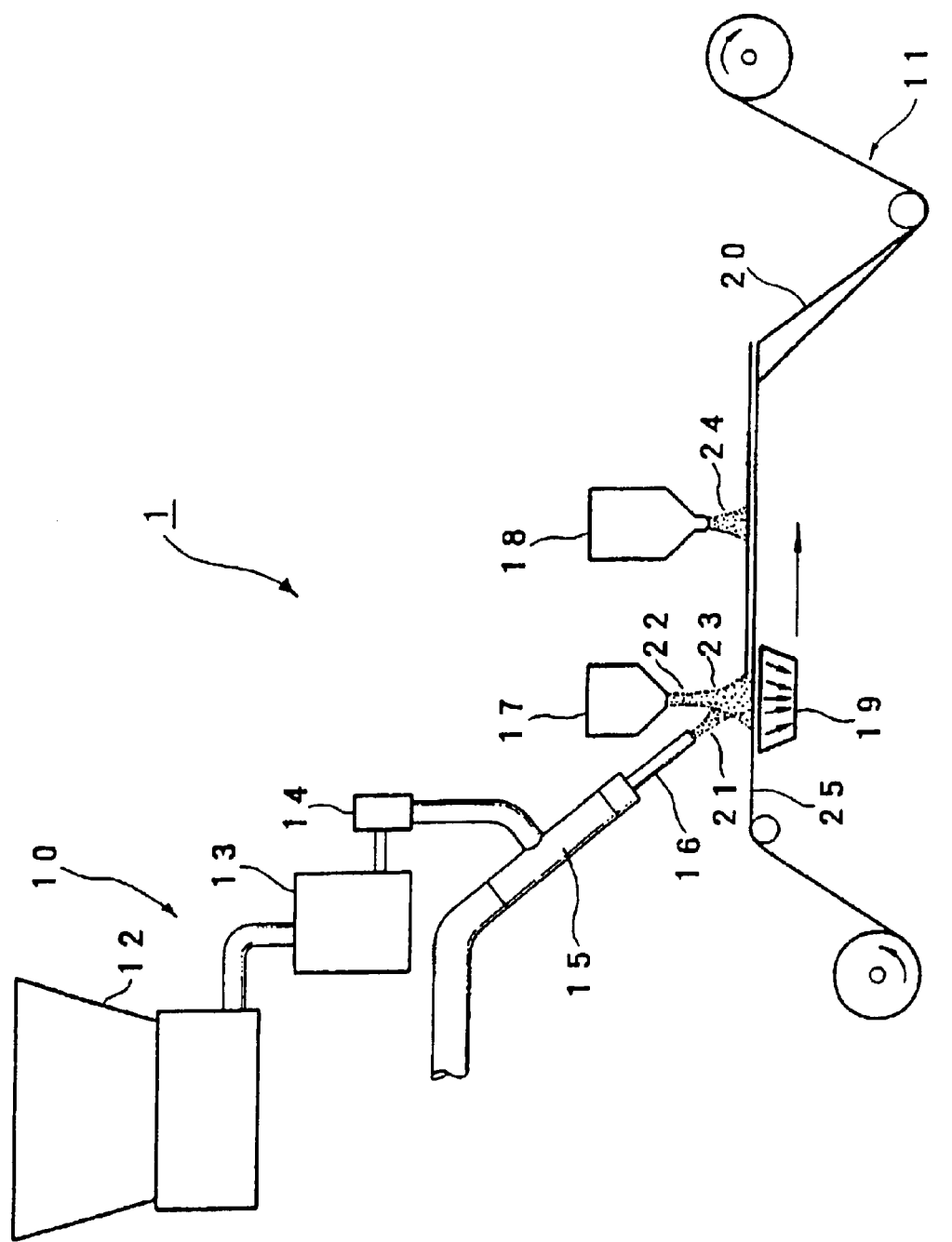
FIG. 1 is a schematic view of an apparatus for making the absorbent materials of the present invention.

The following is a list of definitions for certain terms used herein:

"Comprising" means other steps and other ingredients which do not affect the result can be added. The term encompasses the terms "consisting of" and "consisting essentially of".

"Dry state" means the state of the absorbent material during manufacture.

"Wet state" means the swollen absorbent materials due to absorption of large quantities of liquids such as water, body fluids, industrial fluids and household fluids, when the absorbent materials of the present invention are used in, e.q., a diaper and worn.

"Structural stability" means immobilizing(fixing) the absorbent materials onto the right position in a diaper where first located.

"WAHP" means a water-insoluble absorbent hydrogel-forming polymer.

A. Absorbent Material

The absorbent material of the present invention is capable of absorbing large quantities of liquids such as water, body fluids, industrial fluids and household fluids at a rapid rate and is capable of retaining such fluids under moderate pressures. In particular, the absorbent material of the present invention has an improved structural stability in the dry and wet states, while the absorbent material has a high concentration of WAHPs. Preferably, the absorbent material comprises greater than about 50% by weight of a WAHP. The absorbent materials are no shifting in the dry and wet states.

If one does not adhere the absorbent gelling particles at the desired locations in the dry state, the absorbent gelling particles tend to shift during manufacturing process, resulting in, e.g., clumping of absorbent gelling particles and a lack of uniform distribution of the particles.

If one does not adhere the absorbent gelling particles at the desired locations in the wet state, the particles may shift, resulting in insufficient urine storage capacity in one area and over-capacity in other areas. Subsequently the absorbent article will leak during use(wearing). The shifting of wet absorbent gelling particles of WAHP can cause core shifting and more incidence of gel leakage when in use or wearing, especially from an absorbent article using absorbent materials comprising a high concentration of WAHP.

It is the structural stability in the dry and wet status having a high concentration of WAHP at more than 50% by weight which form the basis for the instant invention over past absorbent materials which have not provided such structural stability in the dry and wet states to the extent now achieved.

The absorbent material of the present invention comprises: (a) absorbent gelling particles comprising a WAHP; (b) a polycationic polymer; (c) glue microfibers; and (d) a carrier layer; wherein the polycationic polymer is bonded to the absorbent gelling particles; and the glue microfibers act as an adhesive between the absorbent gelling particles and the carrier layer.

The present invention in its aspects contemplates the absorbent materials comprising the absorbent gelling particles, the polycationic polymer bonded to the absorbent gelling particles, the glue microfibers dispersed in the absorbent gelling particles and the carrier layer. In particular, its object is to fix the absorbent gelling particles to the desired location of the carrier layer by an adhesive glue microfiber in the dry state and to fix the absorbent gelling particles bonding to the polycationic polymer on the surface, when the absorbent materials contact liquids such as body fluids in the wet state.

The glue microfiber used herein can be meltblown to form fibers that are tacky in at least one step of the manufacture of the absorbent materials. It is possible that the glue microfiber are initially fixed the absorbent gelling particles to the desired location of the absorbent materials during the manufacturing process.

Generally, one can use any polymer as glue microfibers that are sufficiently tacky, to hold onto the particles that contact it, and thereby qualify as an adhesive polymer. Preferably, the melt blown adhesive polymers which can be utilized for forming the absorbent materials include the elastomeric and non-elastomeric polymers. These polymers must be tacky enough to be blown into fiber forms. The tackiness can be modified with the usage of tackifying resins, which include rosin esters, mixed polyalkenes, polyterpenes, waxes, or incorporating carboxylic acid contained polymers or oligomers within the adhesive resin. Also contemplated by the invention are the use of blends of adhesive polymers, or blends of adhesive polymers and other polymers.

Useful elastomeric polymers include polyolefins and blends (e.g., polypropylene, polybutylene, or ethylene-acrylic acid copolymers), ethylenevinyl acetate copolymers, polyamides, polyesters, and reactive polyamide and polyesters.

Pressure sensitive adhesives are also useful for forming the absorbent structure of this invention. They are permanently tacky and do not change their physical state from an initial liquid to a solid after final bond formation. Exemplified elastomeric polymers are ethylenevinyl acetate copolymer, styrene/diene triblock copolymer, poly (vinylether)s, polyacrylates, and silicones. Thermoplastic elastomeric triblock copolymers of the ABA type have great adhesive capability and processing convenience in this invention. The end block (A) in these polymers are plastic in nature with a high glass transition (or melt) temperature, which the block (B) is rubbery. In particular, the styrene-butadiene-styrene, styrene-isoprene-styrene, styrene-ethylene-co-propylene-styrene copolymers are very useful in this invention.

The non-elastomeric polymer may be a non-elastomeric fiber forming resin or blend containing the same. For example, such polymers include polyolefins, non-elastomeric polyamides, cellulosic derived polymers, vinyl chlorides, and polyvinyl alcohols.

In a preferred embodiment of the present invention, the types of elastomeric Styrene-Isoprene-Styrene block copolymers are HL-1358 or Finely H-6752A supplied by Fuller Co. The types of non-elastomeric glue microfiber include polyethyloxazoline, for example XR-2676 (Fuller Co.,), polyvinylpyrolidone, for example H-1716 (Fuller Co.,) and ethylenevinyacetate copolymer, for example HT480 (Fuller Co.,). The glue microfibers comprising polyethyloxazoline would provide the absorbent article comprising the absorbent material of the present invention sufficient structural integrity in the dry state, while in the wet state the polycationic polymers comprising polyethyleneimine are activated to maintain the structural integrity of the absorbent article.

The polycationic polymer used herein is a polymer which has multiple functional groups that are capable of bonding to the surface of the absorbent gelling particles. In a preferred embodiment, an amino-group or iminegroup containing polymer is used as the polycationic polymer. Such polycationic polymers include polyamines, polyimines and mixtures thereof. More preferably, the polyamine is selected from the group consisting of polymers having primary amine groups (e.g., polyvinylamine, polyallylamine), polymers having secondary amine groups (e.g., polyethyleneamines) and polymers having tertiary amine groups (e.g., poly-N, N-dimethylalkyl amine, poly-N-alkylamine). The polyimines preferably used include polyethyleneimines, modified polyethyleneimines crosslinked with epihalohydrine, polyamidoamines grafted with ethyleneimine and mixtures thereof. Other suitable polycationic polymers include modified polyamidoamine grafted with ethyleneimine, polyetheramine, polyvinylamine, polyallylamine, polyamidopolyamine and mixtures thereof.

In a preferred embodiment, the polycationic polymer is a cationic polymer having an average molecular weight of at least about 200, more preferably of at least more than 5,000, and most preferably of more than about 10,000. The polycationic polymers useful in the invention include those polymers having a single maximum value (a peak) in molecular weight distribution, as well as those polycationic polymers having one or more maximum values. The molecular weight distribution can be analyzed by, for example, gel permeation chromatography.

Preferably, the amount of polycationic polymer used in the absorbent material is from about 0.1% to 10% by weight of the absorbent materials.

For providing a high concentration of a WAHP, such as more than 50% by weight of the absorbent material, the polycationic polymer used for the present invention has a concentration of from about 80% to 99% by weight so that it can be tacky by itself. The polycationic polymers having the characteristic of tackiness can be meltblown without glue microfibers, consequently acting as an adhesive between the absorbent gelling particles and the carrier layer. Preferably, the polycationic polymer fiber has a molecular weight of at least about 70,000.

B. Water-insoluble Absorbent Hydrogel-forming Polymer

1. Chemical Composition

The WAHPs useful in the present invention are commonly referred to as "hydrogel-forming", "hydrocolloid", or "superabsorbent" polymers and can include polysaccharides such as carboxymethyl starch, carboxymethyl cellulose, and hydroxypropyl cellulose; nonionic types such as polyvinyl alcohol, and polyvinyl ethers; cationic types such as polyvinyl pyridine, polyvinyl morpholinione, and N,N-dimethylaminoethyl or N,N-diethylaminopropyl acrylates and methacrylates, and the respective quaternary salts thereof. Typically, WAHPs useful in the present invention have a plurality of anionic, functional groups, such as sulfonic acid, and more typically carboxy, groups. Examples of polymers suitable for use herein include those which are prepared from polymerizable, unsaturated, acid-containing monomers. Thus, such monomers include the olefinically unsaturated acids and anhydrides that contain at least one carbon to carbon olefinic double bond. More specifically, these monomers can be selected from olefinically unsaturated carboxylic acids and acid anhydrides, olefinically unsaturated sulfonic acids, and mixtures thereof.

Some non-acid monomers can also be included, preferably in minor amounts, in preparing the WAHPs herein. Such non-acid monomers can include, for example, the water-soluble or water-dispersible esters of the acid-containing monomers, as well as monomers that contain no carboxylic or sulfonic acid groups at all. Optional non-acid monomers can thus include monomers containing the following types of functional groups: carboxylic acid or sulfonic acid esters, hydroxyl groups, amide-groups, amino groups, nitrile groups, quaternary ammonium salt groups, aryl groups (e.g., phenyl groups, such as those derived from styrene monomer). These non-acid monomers are well-known materials and are described in greater detail, for example, in U.S. Pat. No. 4,076,663 (Masuda et. al), issued Feb. 28, 1978, and in U.S. Pat. No. 4,062,817 (Westerman), issued December 13, 1977.

Olefinically unsaturated carboxylic acid and carboxylic acid anhydride monomers include the acrylic acids typified by acrylic acid itself, methacrylic acid, ethacrylic acid, -chloroacrylic acid, -cyanoacrylic acid, -methylacrylic acid (crotonic acid), -phenylacrylic acid, -acryloxypropionic acid, sorbic acid, -chlorosorbic acid, angelic acid, cinnamic acid, p-chlorocinnamic acid, -sterylacrylic acid, itaconic acid, citroconic acid, mesaconic acid, glutaconic acid, aconitic acid, maleic acid, fumaric acid, tricarboxyethylene and maleic acid anhydride.

Olefinically unsaturated sulfonic acid monomers include aliphatic or aromatic vinyl sulfonic acids such as vinylsulfonic acid, allyl sulfonic acid, vinyl toluene sulfonic acid and styrene sulfonic acid; acrylic and methacrylic sulfonic acid such as sulfoethyl acrylate, sulfoethyl methacrylate, sulfopropyl acrylate, sulfopropyl methacrylate, 2-hydroxy-3-methacryloxypropyl sulfonic acid and 2-acrylamide-2-methylpropane sulfonic acid.

Preferred WAHPs for use in the present invention contain carboxy groups. These polymers include hydrolyzed starch-acrylonitrile graft copolymers, partially neutralized hydrolyzed starch-acrylonitrile graft copolyrners, starch-acrylic acid graft copolymers, partially neutralized starch-acrylic acid graft copolymers, saponified vinyl acetate-acrylic ester copolymers, hydrolyzed acrylonitrile or acrylamide copolymers, slightly network crosslinked polymers of any of the foregoing copolymers, partially neutralized polyacrylic acid, and slightly network crosslinked polymers of partially neutralized polyacrylic acid. These polymers can be used either solely or in the form of a mixture of two or more different polymers. Examples of these polymer materials are disclosed in U.S. Pat. No. 4,076,663 (Masuda et. al), issued Feb. 28, 1978, U.S. Pat. No. 4,093,776 (Aoki et. al), issued Jun. 6, 1978, U.S. Pat. No. 4,666,983 (Tsubakimoto et. al), issued May 19, 1987, and U.S. Pat. No. 4,734,478 (Tsubakimoto et. al), issued Mar. 29, 1988.

More preferably polymer materials used in making the WAHPs are slightly network crosslinked polymers of partially neutralized polyacrylic acids and starch derivatives thereof. More preferably still, the WAHPs comprise from about 50 to about 95%, more preferably about 75%, neutralized, slightly network crosslinked, polyacrylic acid (i.e., poly (sodium acrylate/acrylic acid)). Network crosslinking renders the polymer substantially water-insoluble and, in part, determines the absorptive capacity and extractable polymer content characteristics of the WAHPs. Processes for network crosslinking these polymers and typical network crosslinking agents are described in greater detail in U.S. Pat. No. 4,076,663 (Masuda et. al), issued February 28.

Surface crosslinked WAHPs are used in a preferred embodiment of the present invention. They have a higher level of crosslinking in the vicinity of the surface than in the interior. As used herein, "surface" describes the outer-facing boundaries of, e.g., the particle, fiber. For porous WAHPs (e.g., porous particles), exposed internal boundaries can also be included. By a higher level of crosslinking at the surface, it is meant that the level of functional crosslinks for the WAHP in the vicinity of the surface is generally higher than the level of functional crosslinks for the WAHP in the interior.

The gradation in crosslinking from surface to interior can vary, both in depth and profile. Thus, for example, the depth of surface crosslinking can be shallow, with a relatively sharp transition to a lower level of crosslinking. Alternately, for example, the depth of surface crosslinking can be a significant fraction of the dimensions of the WAHP, with a broader transition.

Depending on size, shape, porosity as well as functional considerations, the degree and gradient of surface crosslinking can vary within a given WAHP. For particulate WAHPs, surface crosslinking can vary with particle size, porosity, etc. Depending on variations in surface/volume ratio within the WAHP (e.g., between small and large particles), it is not unusual for the overall level of crosslinking to vary within the material (e.g., be greater for smaller particles).

Surface crosslinking is generally accomplished after the final boundaries of the WAHP is essentially established (e.g., by grinding, extruding, foaming, etc.) However, it is also possible to effect surface crosslinking concurrent with the creation of final boundaries. Furthermore, some additional changes in boundaries can occur even after surface crosslinks are introduced.

The surface crosslinking can be accomplished before or, simultaneously, with the covalent bonding of the polycationic polymer to the surface of the absorbent gelling particles.

While the WAHP is preferably of one type (i.e., homogeneous), mixtures of polymers can also be used in the present invention. For example, mixtures of starch-acrylic acid graft copolymers and slightly network crosslinked polymers of partially neutralized polyacrylic acid can be used in the present invention.

2. Physical Forms

The absorbent gelling particles used in the present invention can have a size, shape and/or morphology varying over a wide range. The absorbent gelling particles may have a large ratio of greatest dimension to smallest dimension (e.g., granules, flakes, pulverulents, interparticle aggregates, interparticle crosslinked aggregates, and the like) and can be in the form of fibers, foams, and the like.

For particles of WAHPs useful in the present invention, the particle size is in the range of from about 10 to about 1000 microns. The WAHPs can also comprise mixtures with low levels of one or more additives, such as, for example, powdered silica, surfactants, celloluse microfiber and the like. The components in this mixture can be physically and/or chemically associated in a form such that the WAHP component and the non-hydrogel-forming polymer additive are not readily physically separable. The WAHPs can be essentially non-porous or have substantial internal porosity.

For particles as described above, particle size is defined as the dimension determined by sieve size analysis. Thus, for example, a particle that is retained on a U.S.A. Standard Testing Sieve with 710 micron openings (e.g., No. 25 U.S. Series Alternate Sieve Designation) is considered to have a size greater than 710 microns; a particle that passes through a sieve with 710 micron openings and is retained on a sieve with 500 micron openings (e.g., No. 35 U.S, Series Alternate Sieve Designation) is considered to have a particle size between 500 and 710 microns; and a particle that passes through a sieve with 500 micron openings is considered to have a size less than 500 microns.

C. Absorbent Article Comprising the Absorbent Materials

The absorbent materials according to the present invention can be used for many purposes in many fields of use. For example, the absorbent material can be used for packing containers; drug delivery devices; wound cleaning devices; bum treatment devices; ion exchange column materials; construction materials; agricultural or horticultural materials such as seed sheets or water-retentive materials; and industrial uses such as sludge or oil dewatering agents, materials for the prevention of dew formation, desiccants, and humidity control materials. In these environments, the absorbent material of the invention can have a number of shapes and sizes. For example, the absorbent material can be in the form of sheets, films, cylinders, blocks or other shaped elements. The absorbent material can comprise a cellulosic material for enhancing absorbency and/or be in a form amenable to these and other applications as described hereinafter.

Because of the unique absorbent properties of the absorbent material of the present invention, it is especially suitable for use as an absorbent core in absorbent articles, especially disposable absorbent articles. As used herein, the term "absorbent article" refers to articles which absorb and contain body fluids and more specifically refers to articles which are placed against or in proximity to the body of the wearer to absorb and contain the various fluids discharged from the body. Additionally, "disposable" absorbent articles are those which are intended to be discarded after a single use (i.e., the original absorbent article in its whole is not intended to be laundered or otherwise restored or reused as an absorbent article, although certain materials or all of the absorbent article may be recycled, reused, or composted).

In general, an absorbent article comprise (a) a liquid pervious topsheet; (b) a liquid impervious backsheet; and (c) an absorbent core positioned between the topsheet and the backsheet wherein the absorbent core comprises at least one absorbent material. As used herein, the term "absorbent core" refers to the component of the absorbent article that is primarily responsible for fluid handling properties of the article, including acquiring, transporting, distributing and storing body fluids. As such, the absorbent core preferably does not include the topsheet or backsheet of the absorbent article.

In a more preferred embodiment, the absorbent core or absorbent member can further comprise fibers or fluff pulp (fibrous or fiber material); more specifically, non-absorbent-gelling fibers. Such fiber material can be used as a reinforcing or absorbent member in the absorbent core, improving fluid handling of the core, as well as serving as a co-absorbent with the absorbent polymers. As used herein, the term "absorbent member" refers to the components of the absorbent core that typically provide one or more fluid handling properties, e.g., fluid acquisition, fluid distribution, fluid transportation, fluid storage, etc. The absorbent member can comprise the entire absorbent core or only a portion of the absorbent core, i.e., the absorbent core can comprise one or more absorbent members.

Any type of fiber material which is suitable for use in conventional absorbent products can be used in the absorbent core or absorbent member herein. Specific examples of such fiber material include cellulose fibers, improved cellulose fibers, rayon, polypropylene, and polyester fibers such as polyethylene terephthalate (DACRON), hydrophilic nylon (HYDROFIL), and the like. Examples of other fiber materials for use in the present invention in addition to some already discussed are hydrophilized hydrophobic fibers, such as surfactant-treated or silica-treated thermoplastic fibers derived, for example, from polyolefins such as polyethylene or polypropylene, polyacrylics, polyamides, polystyrenes, polyurethanes and the like. In fact, hydrophilized hydrophobic fibers which are in and of themselves not very absorbent and which, therefore, do not provide webs of sufficient absorbent capacity to be useful in conventional absorbent structures, are suitable for use in the absorbent core by virtue of their good wicking properties. This is because, in the absorbent core herein, the wicking propensity of the fibers is as important, if not more important, than the absorbent capacity of the fiber material itself due to the high rate of fluid uptake and lack of gel blocking properties of the absorbent core. Synthetic fibers are generally preferred for use herein as the fiber component of the absorbent core. More preferred are polyolefin fibers, preferably polyethylene fibers.

Other cellulosic fiber materials which can be useful in certain absorbent cores or absorbent members herein are chemically stiffened cellulosic fibers. Preferred chemically stiffened cellulosic fibers are the stiffened, twisted, curled cellulosic fibers which can be produced by internally crosslinking cellulose fibers with a crosslinking agent. Suitable stiffened, twisted, curled cellulose fibers useful as the hydrophilic fiber materials herein are described in greater detail in U.S. Pat. No. 4,888,093 (Dean et. al), issued Dec. 19, 1989; U.S. Pat. No. 4,889,596 (Herron et. al), issued Dec. 26, 1989; U.S. Pat. No. 4,889,595 (Schoggen et. al), issued Dec. 26, 1989; U.S. Pat. No. 4,889,597 (Bourbon et. al), issued Dec. 26, 1989; and U.S. Pat. No. 4,898,647 (Moore et al), issued Feb. 6, 1990.

A preferred embodiment of the disposable absorbent article is a diaper. As used herein, the term "diaper" refers to a garment, generally worn by infants and incontinent persons, that is worn about the lower torso of the wearer. A preferred diaper configuration for a diaper comprising an absorbent core is described generally in U.S. Pat. No. 3,860,003 (Buell), issued Jan. 14, 1975. Alternatively preferred configurations for disposable diapers herein are also disclosed in U.S. Pat. No. 4,808,178 (Aziz et. al), issued Feb. 28, 1989; U.S. Pat. No. 4,695,278 (Lawson), issued Sep. 22, 1987; U.S. Pat. No. 4,816,025 (Foreman), issued Mar. 28, 1989; and U.S. Pat. No. 5,151,092 (Buell et. al.), issued Sep. 29, 1992.

Another preferred embodiment of the disposable absorbent article is a catamenial product. Preferred catamenial products comprise a formed-film, apertured topsheet as disclosed in U.S. Pat. No. 4,285,343 (McNair), issued Aug. 25, 1981; U.S. Pat. No. 4,608,047 (Mattingly), issued Aug. 26, 1986; and U.S. Pat. No. 4,687,478 (Van Tilburg), issued Aug. 18, 1987.

Preferred catamenial products can comprise wings, side flaps, and other structures and elements, as described in co-pending, commonly assigned U.S. application Ser. No. 984,071, to Yasuko Morita, entitled "Absorbent Article Having Elasticized Side Flaps", filed Nov. 30, 1992.

It should be understood, however, that the present invention is also applicable to other absorbent articles known commercially by other names, such as incontinent briefs, adult incontinent products, training pants, diaper inserts, facial tissues, paper towels, and the like.

D. Process for Making Absorbent Material

FIG. 1 illustrates a preferred apparatus useful in the process of the present invention. The forming apparatus generally indicated as 1, is composed of a particle applying unit 10, and a carrier layer apparatus 11. The particle applying unit 10 includes an absorbent gelling particles applying unit 12, a glue microfibers applying unit 16 and a polycationic polymer spray unit 17. The absorbent gelling particles are first loaded in, for example, a K-tron screw feeder 12 for continuously feeding absorbent gelling particles to Vibratory feeder 13 and then hopper 14. After absorbent gelling particles are carried away from the outlet of hopper 14 into an eductor 15, absorbent gelling particles leave the nozzle 16 as the first air stream 21 by about 50-psi air stream. The eductor 15 and the nozzle 16 concentrates the absorbent gelling particles into a constant flow in order to inject the absorbent gelling particles through the glue microfibers. Preferably the average diameter of the absorbent gelling particle is usually from about 10 microns to about 1,000 microns. While the absorbent gelling particles are predominately discontinuous, they generally have a length exceeding that normally associated with particles.

The glue microfibers are extruded via glue gun 17 (J&M Co.) with rate between about 0.2 to about 2.0 $Kgcm^{-1} hr^{-1}$ as the second air stream 22. The glue microfibers extrusion thins out when guided through a second air stream. The temperature range is set up enough to solute and spray the glue microfibers. The air gap is preferably kept about 0.18 mm. The second air stream of glue microfibers is controlled to preferably deliver about 10 $g/m^2$ basis weight of the resulting absorbent material and the operation range is preferably from about 3.0 $gm/m^2$ to about 50.0 $gm/m^2$.

The first air stream 21 is merged with the second air stream 22 to form an integrated air stream 23. The integrated air stream 23 is injected onto a carrier layer in mechanical direction, preferably about 70 meter/min. The injection rate of integrated air stream 23 preferably is about 1.0 m/sec which is adjusted to match the carrier unit's speed.

A vacuum conveyor 19 is placed beneath the nozzle 16 and the glue gun 17. As the carrier layer 25 is run through the vacuum conveyor 19, the incoming integrated air stream 23 is attracted and firmly attached to the carrier layer 25. The absorbent gelling particles cover the center line of the carrier layer, preferably at least one half of the width.

A third air stream containing pre-agitated polycationic polymer is located after laydown of the absorbent gelling particles applying unit 18. The third air stream is sprayed onto the absorbent gelling particles attached to the carrier layer and the polycationic polymer bonds to the absorbent gelling particles on the surface. The line speed is controlled preferably at about 8 gm/m².

A folding board 20 is placed adjacent to the polycationic polymer unit 18. The absorbent material comprising the absorbent gelling particles, the glue microfibers, the polycationic polymer and the carrier layer are folded to form an edge closed laminate structure of final width. The laminated product of absorbent material is wound at the end of the line.

The present invention also provides a method for making the absorbent material. The method comprises (a) applying absorbent gelling particles comprising a WAHP onto a carrier layer; (b) applying glue microfibers onto the carrier layer; and (c) applying a polycationic polymer onto the absorbent gelling particles to form a bond between the absorbent gelling particles and the polycationic polymer; wherein the absorbent gelling particles adhere to the glue microfibers prior to the glue microfibers adhering to the carrier layer.

In one embodiment, the method further comprises the step of dispersing cellulose fibers into the absorbent gelling particles, wherein the glue microfibers act as an adhesive between the cellulose fibers and the absorbent gelling particles.

In a preferred embodiment, the absorbent gelling particles are applied via a first air stream on a carrier layer.

In more preferred embodiment, the glue microfibers are applied via the second air stream. The second air stream comprising glue microfibers preferably has a temperature of from about 10° C. to about 400° C.

In a preferred embodiment, the polycationic polymer is applied via the third air stream. The third air stream comprising the polycationic polymer is used as a solution having a concentration preferably from about 0.1% to about 10% by weight.

The solution containing the polycationic polymer is then applied to a plurality of the absorbent gelling particles. In particular, at least two, preferably all, of the absorbent gelling particles have at least some portion covered with the solution. In a preferred embodiment, at least 70% of the surface area of the gelling particles are covered with the solution applied thereon. The solution can be applied using any of the various techniques and apparatus well known in the art which are suitable for applying a solution to a material including coating, dumping, pouring, dropping, spraying, atomizing, condensing, or immersing the solution onto the absorbent gelling particles. After the polycationic polymer is applied, preferably greater than about 90% of the surface area of the gelling particles is covered with the solution.

In a preferred embodiment, the method further comprises the step of heating the resulting material of step (c) at a temperature of from about 50° C. to about 300° C. so as to covalently bond the polycationic polymer to the WAHP of the absorbent gelling particles.

In a preferred embodiment, the polycationic polymer are reacted with the absorbent gelling particles such that the polyeationic polymer becomes covalently bonded to the absorbent gelling particles at the surface area of the absorbent gelling particles. More preferably, the covalent bonds are made between the surface-located carboxy groups of the absorbent gelling particles and the amino groups of the polycationic polymer. Preferably, at least about 80% more preferably more than about 90% by weight of the polycationic polymer is covalently bonded to the absorbent gelling particles. When supplied with higher thermal energy, the absorbent articles comprising the absorbent material have more fluid permeable. With the improved fluid permeability the spreading of, e.g., urine throughout the absorbent articles comprising the absorbent material is increased, and therefore the absorbent gelling particles fluid absorption efficiency can be raised.

The present invention also relates to a method of making an absorbent material. The method comprises (a) forming a first air stream comprising absorbent gelling particles comprising a WAHP; (b) forming a second air stream comprising glue microfibers; (c) merging the second air stream with the first air stream to form an integrated air stream comprising a through mixture of the glue microfibers and the absorbent gelling particles; (d) directing the integrated air stream onto a carrier layer, (e) forming a third air stream comprising a polycationic polymer; and (f) directing the third air stream onto the carrier layer so the polycationic polymer bonds to the absorbent gelling particles.

Preferably, the method of forming an absorbent material comprises (a) forming a first air stream comprising absorbent gelling particles comprising a WAHP; (b) forming a second air stream comprising a polycationic polymer, (c) merging the second air stream with the first air stream to form an integrated air stream, wherein the polycationic polymer bonds to the absorbent gelling particles; (d) forming a third air stream comprising glue microfibers; (e) merging the integrated air stream with the third air stream to form a mixture air stream; and (f) directing the mixture air stream onto a carrier layer so the absorbent gelling particles bonded to the polycationic polymer adhere to the glue microfibers, and the glue microfibers adhere to the carrier layer.

In a more preferred embodiment, the second air stream is formed a temperature of at least about 400° C. and about 50 psi air pressure at sonic velocity.

In another embodiment, the method comprises (a) applying polycationic polymer fibers comprising a polycationic polymer having a concentration of from about 80% to about 99% by weight onto absorbent gelling particles comprising a WAHP; and (b) applying the absorbent gelling particles onto a carrier layer; wherein the polycationic polymer fibers act as an adhesive between the absorbent gelling particles and the carrier layer. Preferably, the polycationic polymer fiber has the molecular weight of at least about 70,000.

In a preferred embodiment, the polycationic polymer fibers form a first air stream containing the polycationic polymer fibers and the absorbent gelling particles from the second air stream to form an integrated air stream containing a thorough mixture of the polycationic polymer fibers and the absorbent gelling particles.

In a more preferred embodiment, the method comprises (a) forming a first air stream containing polycationic polymer fibers; (b) forming a second air stream containing absorbent gelling particles comprising a WAHP; (c) merging the second air stream with the first air stream to form an integrated air stream, wherein the polycationic polymer fibers bond to the absorbent gelling particles; and (d) directing the integrated air stream onto a carrier layer so that the absorbent gelling particles bond to the polycationic polymer fibers on the carrier layer.

E. Test Methods

1. Synthetic Urine

The specific synthetic urine used in the test methods set forth herein is referred to as "Synthetic Urine". The Synthetic Urine is commonly known as Jayco SynUrine or Jayco Synthetic Urine and is available from Jayco Pharmaceuticals Company of Camp Hill, Pa. The formula for the Synthetic Urine is: 2.0 g/l of KCl; 2.0 g/l of $Na_2SO_4$; 0.85 g/l of $(NH_4)H_2PO_4$; 0.15 g/l $(NH_4)H_2PO_4$; 0.19 g/l of $CaCl_2$ and 0.23 g/l of $MgCl_2$. All of the chemicals are of reagent grade. The PH of the Synthetic Urine is in the range of 6.0 to 6.4.

2. Wet Burst Strength Measurement

The standard burst test program measures load, deflection and energy at peak load, and fail load at test end. The purpose of this test is to evaluate the gram force of a absorbent-gelling-particle-contained laminate structure after subjecting to a constant loading of synthetic urine. Laminate samples with a dimension of 10 cm×10 cm and of 310 gm/m2 absorbent gelling particle basis weights, typically weigh at 3.6±0.3 gm and are allowed to soak in 70 mL of synthetic urine. Synthetic urine is fully absorbed by the absorbent-gelling-particle contained laminate, with 20 times synthetic urine loading of its original weight A burst tester, Thwing-Albert instrument Co. No. 177-1-B, is used to measure the gram force needed to puncture the 20 time's synthetic urine-loaded laminate samples. The sample holder is a plexi glass disk of 4.5-inch diameter and 0.125 inch of thickness, and with a hole of 0.75 inch diameter in the center of plexiglass. A stainless ball head of 0.25-inch diameter is used to puncture the samples.

3. Tea Bag Gel Volume

Gel volume of a WAHP is defined as its retention absorbent capacity after swollen in an excess of Jaycee Synthetic Urine. It provides a measure of the maximum absorbent capacity of the polymer under conditions of use where the pressures on the polymer are relatively low. Gel volume is determined by centrifuge capacity method described below by using the Jaycee Synthetic Urine. The gel volume is calculated on a dry-weight basis. The dry weight used in the gel volume calculation is determined by oven drying the WAHP at 105° C. for three hours. All of the chemicals are of reagent grade. The pH of the Jaycee Synthetic Urine is in the range of 8.0 to 6.4.

Heat-sealable tea-bag paper is cut into 6 cm×12 cm, folded in half lengthwise and sealed close to the edge along two sides with a T-bar sealer to produce 6 cm×6 cm tea bag squares. 0.200(±0.005) gm of a WAHP is transferred into a tea-bag, and the top of the bag is sealed at its edge. The top of an empty tea-bag is sealed and is used as a blank. Approximately 300 ml of Jayco Synthetic Urine is poured into a 1,000 ml beaker, and the tea-bag containing WAHP and the blank are submerged into the beaker. After being soaked for 30 minutes, the blank and the WAHP-filled tea bag are removed from the solution by using tongs. A centrifuge (H-122 type, Kokusan Enshinki Co. Ltd., Tokyo, Japan) with a direct read tachometer, electric timer is used for this measurement. The sample tea bags and the blank tea bags are positioned in the centrifuge basket and centrifuged at 1100 rpm for three minutes. Gel volume is calculated as follows:

Gel volume $(g/g)=(Ws-Wb-Wo)/Wo$ wherein Ws is the sample tea bag weight after centrifuge, Wb is the blank tea bag weight after centrifuge, Wo is the WAHP weight (0.200 g).

The average of at least two determinations should be reported.

4. Acquisition Speed and Re-wet Test

The Acquisition Speed and Rewetness, which are the laminate production properties comprising this absorbent material made according to present invention, are evaluated in diapers. The typical diaper design includes airfilt as the acquisition layer and the laminate production as fluid storage core of at least 310 gm/m2 absorbent gelling particle basis weight. The acquisition speed and rewet measurements are performed with 0.30 psi external pressure in a flat configuration. After continuous loading of 200 mL synthetic urine, several pieces of fitter papers are placed on the wet pad and allowed to soak for 30 min under 0.40 psi. The rewet values, as measured from the weight increase of filter paper, are summed up from front, middle, to back part of diaper.

F. EXAMPLES

The following examples are presented for purposes of illustrating various aspects of the absorbent material of the invention and are not intended as limiting the scope of the appended claims in any way.

A composite in accordance with the present invention is prepared on a process line for laminate production illustrated in FIG. 1.

All raw materials used in this example are obtained from commercial sources. Styrene-Isoprene-Styrene block copolymer (HL-1358-XZP) produced by H.B. Fuller Co. is used as a glue microfiber, and is heated and kept at least 350° C. during laminate production process. L76lf produced by Nippon Shokubai Co. Ltd. is used as absorbent gelling particles, and has particle size distribution ranging from 300 $\mu$m to 600 $\mu$m. The Polyethyleneimine produced by Wako Chem Co., is used as a polycationic polymer, and is a 30% solid and has molecular weight of 70,000 Daltons. A tissue produced by Havix Company LTD is used as a wet laid tissue of 18 gms and has the tensile strength of 1.1 Kg/in in mechanical direction.

The properties of the absorbent material, Wet Burst Strength (BBS) and absorbent capacity (GV) are evaluated and presented in Table 1. In a diaper including the absorbent material of present invention. Acquisition speed and Rewet performances are evaluated and presented in Table 2.

Example 1

L76lf is prepared in K-tron screw feeder. L76lf is loaded in a K-tron screw feeder for continuously feeding L76lf into a vibrator feeder and then a hopper. A compressed air stream is kept at 50 psi air pressure. L76lf is carried away from the outlet of the hopper into an educator and is combined with the compressed air stream, so as to provide a first air stream. Injection rate of the first air stream of L76lf is kept about 1.0 $msec^{-1}$ which is adjusted to match the web line speed.

Styrene-Isoprene-Styrene block copolymer (HL-1358-XZP), is prepared in the apparatus of glue gun (J&M Co.). HL-1358-XZP is extruded through glue gun at a rate between about 0.2 to about 2.0 $Kgcm^{-1} hr^{-1}$. The air gap of the glue gun is kept at about 0.18 mm, as the glue block-copolymer becomes thin fibers.

The extruded HL-1358-XZP is combined with an air stream, so as to provide a second air stream. The second air stream is kept at a temperature of about 400° C. and about 50 psi air pressure at about sonic velocity. The second air stream of HL-1358-XZP is controlled to deliver 10 g/m² basis weight of the laminate production. The operation range of the second air stream can be between about 3.0 gm/m² and about 50.0 gm/m².

The first air stream of L76lf is subsequently injected through the second air stream of HL-1358-XZP, to form an integrated air stream, onto a vacuum conveyer.

The vacuum conveyor is placed beneath the glue gun and the educator.

At the same time, a tissue is introduced to the vacuum conveyor at a typical speed of about 70 meter/min. As the tissue is run over the vacuum conveyor, the incoming integrated air stream is attracted and firmly attached to the tissue. The tissue width is at least about 23 cm and a coverage width of the integrated air stream is at least about 9.50 cm.

A polyethyleneimine is dissolved in distilled water at a concentration of from about 10 to about 20% by weight. A third air stream spray is forwarded an air pressure spray system (B⅛ BAU–SS+SUV 67–SS from Spraying System Co. of 0.5–1.2 Kg/cm$^2$) containing a pre-agitated solution of polyethyleneimine and water is located after the integrated air stream containing HL-1358-XZP and L76lf laydown. According to the line speed, the speed of spraying and the level of polyethyleneimine solution is controlled at 8 gm/m2, which is equal to about 2.0% by weight of the laminate production.

A folding board is placed next to the third air stream spray of polyethyleneimine solution. Tissue, L76lf, HL-1358-XZP and polyethyleneimine are folded to form an edge closed laminate structure of about 10 cm final width. The laminate production is wound at the end of the line. The thickness of a formed laminate of about 310 gm/m2 absorbent gelling particle is about 1.3 mm.

The laminate production properties comprising this absorbent material made according to this example are evaluated. The Wet Burst Strength and The Tea Bag gel Volume is 61 gm and 33 g/g. The results surprisingly illustrate the higher gel strength (BBS) and high absorbent capacity (GV) achieved by the absorbent material according to the present invention.

Example 2

The basic composition of sample is similar to Example 1, except no third air stream spray of polyethyleneimine additive is used.

The laminate production properties comprising this absorbent material made according to this example are evaluated. The Wet Burst Strength and The Tea Bag gel Volume is 25 gm and 35 g/g.

Example 3

In this example, the basic composition of sample is similar to Example 1, except as set forth below.

(1) "URIC absorbent gelling particle" is prepared in K-tron screw feeder for use in the first air stream. "URIC absorbent gelling particle" is an absorbent gelling particle having improved absorbent property by the absorbent property modification polymer, such as the polycationic polymer, bonded to the absorbent gelling particles.
(2) There is no third air stream spray.

The laminate production properties comprising this absorbent material made according to this example are evaluated. The Wet Burst Strength and The Tea Bag gel Volume is 45 gm and 31 g/g. The results surprisingly illustrate the higher gel strength (BBS) and high absorbent capacity (GV) achieved by the absorbent material according to the present invention.

Example 4

The basic composition of the sample is similar to Example 1, except no second air stream of the thermoplastic polymeric microfiber and the third air stream spray of polyethyleneimine additive are used.

The laminate production properties comprising this, absorbent material made according to this example are evaluated. The Wet Burst Strength and The Tea Bag gel Volume is 0 gm and 38 g/g.

TABLE 1

Tea bag gel volume and effects on wet strength by adding polyethyleneimine

| Samples | | Polyethyleneimine (%) | Wet Burst Strength (gm) | Tea bag gel volume (g/g) |
|---|---|---|---|---|
| Sample #1 | Polycationic polymer is added in situ during laminate making process. | 2 | 61 | 33 |
| Sample #2 | No polycationic polymer is included. | 0 | 25 | 35 |
| Sample #3 | Polycationic polymer is added during absorbent gelling particle making process. Subsequently this absorbent gelling particle is used to make laminate structure. | 2 | 45 | 31 |
| Sample #4 | No glue microfiber. | 0 | 0 | 38 |

The acquisition speeds and rewet values are evaluated in a diaper. The diaper is made of by laminate production comprising the absorbent material according to above examples. The properties of the diaper are evaluated and presented in Table 2.

TABLE 2

Acquisition and rewet performances of the invention in diaper application.

| Samples | Acquisition Speed (sec) 50 mL, 100 mL, 150 mL, 200mL of synthetic urine loading | | | | Pad Rewet (gm) at 200 mL loading of synthetic urine |
|---|---|---|---|---|---|
| Sample #1 | 20 | 31 | 35 | 43 | 0.50 |
| Sample #2 | 18 | 28 | 39 | 55 | 0.50 |
| Sample #3 | 16 | 20 | 23 | 28 | 0.50 |

Diapers of this invention (the sample #1 and #3) show faster acquisition speeds at high urine loading, e.g., urine volume levels of at least 150 mL than the Sample #2. The improved acquisition speeds are caused by faster fluid transportation among the well-bonded absorbent gelling particle particulate in the wet state. In Sample #3, where absorbent gelling particle is treated with polyethyleneimine alternatively during absorbent gelling particle production process, the laminate shows even faster acquisition speeds. The degree of bonding forces in Sample #3 is higher than that of Sample #1. Also shown in Table-2, the rewet values of the invention maintain control diaper that is used to the absorbent material of no polycationic polymer.

All publications, patent applications, and issued patents mentioned hereinabove are hereby incorporated in their entirety by reference.

It is understood that the examples and embodiments described herein are for illustrative purposes only and that various modifications or changes in light thereof will be suggested to one skilled in the art and are to be included in the spirit and purview of this application and scope of the appended claims.

What is claimed is:

1. An absorbent material comprising:
   (a) absorbent gelling particles comprising a water-insoluble absorbent hydrogel forming polymer;
   (b) a polycationic polymer;
   (c) from about 1% to about 10% of glue microfibers selected from the group consisting of:
      i) tackifier modified polymers,
      ii) pressure sensitive adhesives, and
      iii) mixtures thereof; and
   (d) a carrier layer, wherein the polycationic polymer is dispersed on the glue microfibers and is bonded to the absorbent gelling particles; and wherein at least a portion of the absorbent gelling particles, deposited onto the carrier layer, are fixed to the surface of the carrier layer and a majority of individual absorbent gelling particles are directly joined to an adjacent absorbent gelling particle by the glue microfibers in the dry state and wherein the glue microfibers are melt-blown fibers.

2. The absorbent material of claim 1, wherein the carrier layer is selected from the group consisting of a woven material and a nonwoven material.

3. The absorbent material of claim 1, further comprising cellulose fibers dispersed in the absorbent gelling particles, wherein the cellulose fibers are adhered to the absorbent gelling particles by the glue microfibers.

4. The absorbent material of claim 3, wherein the glue microfiber is selected from the group consisting of an elastomeric microfiber and a non-elastomeric microfiber.

5. The absorbent material of claim 4, wherein the elastomeric microfiber is a thermoplastic polymeric meltblown microfiber.

6. The absorbent material of claim 5, wherein the thermoplastic polymeric meltblown microfiber is an elastomeric Styrene-Isoprene-Styrene block copolymer.

7. The absorbent material of claim 4, wherein the non-elastomeric microfiber is selected from the group consisting water-soluble microfiber and water-insoluble microfiber.

8. The absorbent material of claim 7, wherein the water-soluble microfiber is selected from the group consisting of polyethyloxazoline, polyvinylpyrolidone, ethylenevinylacetate copolymer glue and mixtures thereof.

9. The absorbent material of claim 1, wherein the polycationic polymer is selected from the group consisting of polyamines, polyimines, and mixtures thereof.

10. The absorbent material of claim 9 wherein the polyamine is selected from the group consisting of:
    (a) polymers having primary amine groups;
    (b) polymers having secondary amine groups; and
    (c) polymers having tertiary amine groups.

11. The absorbent material of claim 10, wherein the primary amine is selected from the group consisting of a polyvinylamine, a polyallylamine and mixtures thereof.

12. The absorbent material of claim 10, wherein the secondary amine is a polyethyleneamine.

13. The absorbent material of claim 10, wherein the tertiary amine is selected from the group consisting of a poly N,N-dimethylalkyl amine, a poly-N-alkylamine, and mixtures thereof.

14. The absorbent material of claim 9, wherein the polyimine is selected from the group consisting of a polyethyleneimine, modified polyethyleneimines crosslinked with epihalohydrine, polyamidoamine grafted with ethyleneimine and mixtures thereof.

15. The absorbent material of claim 1, wherein the absorbent gelling particles have an average particle size in the range of from about 10 $\mu$m to about 1000 $\mu$m.

16. The absorbent material of claim 1, wherein the polycationic polymer chemically crosslinks to the water-insoluble absorbent hydrogel-forming polymer of absorbent gelling particles.

17. The absorbent material of claim 1, wherein the absorbent material comprises from about 50% to about 90% of the absorbent gelling particle, from about 0.1% to about 10% of the polycationic polymer; and from about 5% to about 50% of the carrier layer by weight.

18. The absorbent material of claim 1, wherein the polycationic polymer have a molecular weight of at least about 70,000.

19. An absorbent article comprising:
    (a) a liquid pervious topsheet;
    (b) a liquid impervious backsheet; and
    (c) an absorbent core positioned between the topsheet and the backsheet, wherein the absorbent core comprises the absorbent material of claim 1.

20. An absorbent article comprising the absorbent material of claim 1.

21. The absorbent article of claim 20, wherein the absorbent article is a diaper.

22. The absorbent article of claim 20, wherein the absorbent article is a catamenial product.

* * * * *

UNITED STATES PATENT AND TRADEMARK OFFICE
CERTIFICATE OF CORRECTION

PATENT NO. : 6,730,387 B2
DATED : May 4, 2004
INVENTOR(S) : Ebrahim Rezai et al.

It is certified that error appears in the above-identified patent and that said Letters Patent is hereby corrected as shown below:

Column 8,
Line 44, delete "bum" and insert -- burn --.

Column 11,
Line 63, delete "polyeationic" and insert -- polycationic --.

Column 14,
Line 4, delete "fitter" and insert -- filter --.

Signed and Sealed this

Thirty-first Day of January, 2006

JON W. DUDAS
*Director of the United States Patent and Trademark Office*